US012672976B2

(12) United States Patent
 Sandahl et al.

(10) Patent No.: US 12,672,976 B2
(45) Date of Patent: Jul. 7, 2026

(54) HINGE ASSEMBLY

(71) Applicant: Ossur Iceland ehf, Reykjavik (IS)

(72) Inventors: David Sandahl, Reykjavik (IS); Tomas Njalsson, Reykjavik (IS); Valgeir Petursson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 44 days.

(21) Appl. No.: 18/956,505

(22) Filed: Nov. 22, 2024

(65) Prior Publication Data

US 2025/0177180 A1 Jun. 5, 2025

Related U.S. Application Data

(60) Provisional application No. 63/605,261, filed on Dec. 1, 2023.

(51) Int. Cl.
 *A61F 5/01* (2006.01)
(52) U.S. Cl.
 CPC .... *A61F 5/0123* (2013.01); *A61F 2005/0137* (2013.01); *A61F 2005/0139* (2013.01)
(58) Field of Classification Search
 CPC ................. A61F 5/0123; A61F 5/0125; A61F 2005/0137; A61F 2005/0139
 See application file for complete search history.

(56) References Cited

U.S. PATENT DOCUMENTS

| | | | |
|---|---|---|---|
| 1,390,915 A | 9/1921 | Julius | |
| 2,531,486 A | 11/1950 | Weber | |

| | | | |
|---|---|---|---|
| 2,883,982 A | 4/1959 | Rainey | |
| 3,030,634 A | 4/1962 | Bair | |
| 3,099,488 A | 7/1963 | Eckenrod | |
| 3,259,910 A | 7/1966 | Gustave | |
| 3,387,305 A | 6/1968 | Shafer | |
| 3,669,105 A | 6/1972 | Castiglia | |
| 3,779,654 A | 12/1973 | Horne | |
| 3,785,372 A | 1/1974 | Craig | |
| 3,817,244 A | 6/1974 | Taylor | |
| 3,900,898 A | 8/1975 | Ackerman | |

(Continued)

FOREIGN PATENT DOCUMENTS

| | | |
|---|---|---|
| AU | 2005203062 A1 | 8/2005 |
| DE | 29823435 U1 | 7/1999 |

(Continued)

OTHER PUBLICATIONS

International Search Report from Corresponding PCT Application No. PCT/US2024/057042, Feb. 11, 2025.

(Continued)

*Primary Examiner* — Jeffrey O'Brien

(74) *Attorney, Agent, or Firm* — Workman Nydegger

(57) ABSTRACT

A hinge assembly with improved durability is provided with a first hinge arm with a first end portion, a second hinge arm with a second end portion, and a wear insert integrated with the second end portion. A gear segment of the first end portion is integrally formed from the first hinge arm and composed of a first material. The wear insert of the second end portion is distinctly formed from the second hinge arm. The wear insert is formed of a second material, while the second hinge arm is formed of the first material.

19 Claims, 5 Drawing Sheets

(56) References Cited

U.S. PATENT DOCUMENTS

| | | | |
|---|---|---|---|
| 3,901,223 A | 8/1975 | May | |
| 3,902,482 A | 9/1975 | Taylor | |
| 3,923,047 A | 12/1975 | Chant | |
| 3,928,872 A | 12/1975 | Johnson | |
| 3,958,569 A | 5/1976 | Vosburgh | |
| 4,068,312 A | 1/1978 | Ledesma | |
| 4,088,130 A | 5/1978 | Applegate | |
| 4,136,404 A | 1/1979 | Lange | |
| 4,169,467 A | 10/1979 | Bel et al. | |
| 4,241,730 A | 12/1980 | Helfet | |
| 4,271,831 A | 6/1981 | Deibert | |
| 4,361,142 A | 11/1982 | Lewis et al. | |
| 4,372,298 A | 2/1983 | Lerman | |
| 4,381,769 A | 5/1983 | Prahl | |
| D269,379 S | 6/1983 | Bledsoe | |
| 4,407,276 A | 10/1983 | Bledsoe | |
| 4,428,369 A | 1/1984 | Peckham et al. | |
| 4,487,200 A | 12/1984 | Feanny et al. | |
| 4,489,718 A | 12/1984 | Martin | |
| 4,493,316 A | 1/1985 | Reed et al. | |
| 4,494,534 A | 1/1985 | Hutson | |
| 4,503,846 A | 3/1985 | Martin | |
| 4,520,804 A | 6/1985 | DiGeorge | |
| 4,523,585 A | 6/1985 | Lamb et al. | |
| 4,524,764 A | 6/1985 | Miller et al. | |
| 4,554,913 A | 11/1985 | Womack et al. | |
| D284,702 S | 7/1986 | Castillo | |
| 4,599,748 A | 7/1986 | Garcia | |
| 4,599,998 A | 7/1986 | Castillo | |
| 4,603,690 A | 8/1986 | Skeen | |
| 4,614,181 A | 9/1986 | Karlsson | |
| 4,614,454 A | 9/1986 | Kassai | |
| 4,620,532 A | 11/1986 | Houswerth | |
| 4,621,624 A | 11/1986 | Rayboy | |
| 4,628,916 A | 12/1986 | Lerman et al. | |
| 4,633,867 A | 1/1987 | Kausek et al. | |
| 4,665,905 A | 5/1987 | Brown | |
| 4,681,097 A | 7/1987 | Pansiera | |
| 4,697,583 A | 10/1987 | Mason et al. | |
| 4,699,129 A | 10/1987 | Aaserude et al. | |
| 4,715,363 A | 12/1987 | Detty | |
| 4,723,539 A | 2/1988 | Townsend | |
| 4,732,143 A | 3/1988 | Kausek et al. | |
| 4,753,240 A | 6/1988 | Sparks | |
| D298,568 S | 11/1988 | Womack et al. | |
| 4,791,916 A | 12/1988 | Paez | |
| 4,802,372 A | 2/1989 | Harrod et al. | |
| 4,803,975 A | 2/1989 | Meyers | |
| 4,821,707 A | 4/1989 | Audette | |
| 4,854,308 A | 8/1989 | Drillio | |
| 4,856,501 A | 8/1989 | Castillo et al. | |
| 4,886,054 A | 12/1989 | Castillo et al. | |
| 4,890,607 A | 1/1990 | Townsend | |
| 4,938,207 A | 7/1990 | Vargo | |
| 4,940,044 A | 7/1990 | Castillo | |
| 4,961,416 A | 10/1990 | Moore et al. | |
| 4,964,402 A | 10/1990 | Grim et al. | |
| 4,966,133 A | 10/1990 | Kausek | |
| 4,986,264 A | 1/1991 | Miller | |
| 4,991,571 A | 2/1991 | Kausek | |
| 5,000,169 A | 3/1991 | Swicegood et al. | |
| 5,005,565 A | 4/1991 | Fratesi | |
| 5,022,391 A | 6/1991 | Weidenburner | |
| 5,025,782 A | 6/1991 | Salerno | |
| D318,736 S | 7/1991 | Castillo | |
| 5,031,606 A | 7/1991 | Ring, Sr. | |
| 5,038,763 A | 8/1991 | Wiggins | |
| 5,038,765 A | 8/1991 | Young et al. | |
| 5,062,858 A | 11/1991 | Broeck et al. | |
| 5,063,916 A | 11/1991 | France et al. | |
| 5,072,970 A | 12/1991 | Dandy et al. | |
| 5,078,127 A | 1/1992 | Daneman et al. | |
| 5,107,823 A | 4/1992 | Fratesi | |
| 5,121,742 A * | 6/1992 | Engen | A61F 5/0125 602/26 |
| 5,131,684 A | 7/1992 | Dandy et al. | |
| 5,131,685 A | 7/1992 | Dandy et al. | |
| 5,135,469 A | 8/1992 | Castillo | |
| 5,168,865 A | 12/1992 | Radcliffe et al. | |
| 5,222,733 A | 6/1993 | Brunty | |
| 5,230,696 A | 7/1993 | Silver et al. | |
| 5,230,697 A | 7/1993 | Castillo et al. | |
| 5,259,832 A | 11/1993 | Townsend et al. | |
| 5,288,287 A | 2/1994 | Castillo et al. | |
| D346,028 S | 4/1994 | Lengyel | |
| 5,333,604 A | 8/1994 | Green et al. | |
| 5,334,135 A | 8/1994 | Grim et al. | |
| 5,356,370 A | 10/1994 | Fleming | |
| 5,372,572 A | 12/1994 | Tamagni | |
| 5,376,134 A | 12/1994 | Biedermann | |
| RE34,818 E | 1/1995 | Daneman et al. | |
| D357,070 S | 4/1995 | Castillo | |
| 5,403,002 A | 4/1995 | Brunty | |
| 5,421,810 A * | 6/1995 | Davis | A61F 5/0193 602/26 |
| 5,443,444 A * | 8/1995 | Pruyssers | A61F 5/0123 602/5 |
| 5,445,602 A | 8/1995 | Grim et al. | |
| D367,536 S | 2/1996 | Kilbey | |
| 5,490,822 A | 2/1996 | Biedermann | |
| D370,261 S | 5/1996 | Kilbey | |
| D370,533 S | 6/1996 | Kilbey | |
| 5,554,104 A | 9/1996 | Grim | |
| 5,641,322 A | 6/1997 | Silver et al. | |
| 5,658,243 A | 8/1997 | Miller et al. | |
| 5,662,596 A | 9/1997 | Young | |
| 5,674,188 A | 10/1997 | Young | |
| 5,695,452 A | 12/1997 | Grim et al. | |
| 5,713,837 A | 2/1998 | Grim et al. | |
| 5,716,335 A | 2/1998 | Iglesias et al. | |
| 5,741,221 A | 4/1998 | Wetz et al. | |
| 5,743,865 A | 4/1998 | Townsend | |
| 5,766,140 A | 6/1998 | Tillinghast et al. | |
| 5,772,618 A * | 6/1998 | Mason | A61F 5/0123 602/26 |
| 5,782,780 A | 7/1998 | Mason et al. | |
| 5,792,084 A | 8/1998 | Wilson et al. | |
| 5,794,261 A | 8/1998 | Hefling | |
| 5,807,294 A | 9/1998 | Cawley et al. | |
| 5,823,931 A | 10/1998 | Gilmour | |
| 5,865,777 A | 2/1999 | Detty | |
| 5,891,071 A | 4/1999 | Stearns et al. | |
| 5,921,946 A | 7/1999 | Tillinghast et al. | |
| 5,951,504 A | 9/1999 | Iglesias et al. | |
| D416,624 S | 11/1999 | Nauert | |
| 6,001,075 A | 12/1999 | Clemens et al. | |
| 6,024,712 A | 2/2000 | Iglesias et al. | |
| 6,027,466 A | 2/2000 | Diefenbacher et al. | |
| 6,074,355 A | 6/2000 | Bartlett | |
| D431,295 S | 9/2000 | Rothenberg | |
| 6,129,689 A | 10/2000 | Dibello | |
| D433,756 S | 11/2000 | Castillo | |
| 6,205,583 B1 | 3/2001 | Beland | |
| RE37,297 E | 7/2001 | Smith, III | |
| 6,290,664 B1 | 9/2001 | Nauert | |
| D451,644 S | 12/2001 | Fujimoto et al. | |
| 6,393,610 B1 | 5/2002 | Parks | |
| 6,402,711 B1 | 6/2002 | Nauert | |
| D463,886 S | 10/2002 | Cantu, Jr. | |
| 6,461,318 B2 | 10/2002 | Freeman et al. | |
| 6,464,657 B1 | 10/2002 | Castillo | |
| 6,500,139 B1 | 12/2002 | Townsend et al. | |
| 6,527,733 B1 * | 3/2003 | Ceriani | A61F 5/0123 602/26 |
| 6,540,709 B1 | 4/2003 | Smits | |
| 6,676,617 B1 | 1/2004 | Miller | |
| 6,689,080 B2 | 2/2004 | Castillo | |
| 6,736,567 B1 | 5/2004 | Dibello | |
| 6,740,054 B2 | 5/2004 | Stearns | |
| 6,752,775 B2 | 6/2004 | Seligman et al. | |
| 6,793,641 B2 | 9/2004 | Freeman et al. | |
| 6,796,951 B2 | 9/2004 | Freeman et al. | |
| D501,690 S | 2/2005 | Chen | |
| 6,875,187 B2 | 4/2005 | Castillo | |

(56) References Cited

U.S. PATENT DOCUMENTS

| | | | |
|---|---|---|---|
| 6,878,126 | B2 | 4/2005 | Nelson et al. |
| D504,981 | S | 5/2005 | Vanderhoef |
| 6,890,314 | B2 | 5/2005 | Seligman |
| 6,988,999 | B1 | 1/2006 | Lin |
| D517,248 | S | 3/2006 | Castillo et al. |
| 7,044,925 | B2 | 5/2006 | Castillo et al. |
| 7,059,329 | B2 | 6/2006 | Mason et al. |
| 7,189,212 | B2 | 3/2007 | Popp et al. |
| 7,235,058 | B2 | 6/2007 | Doty et al. |
| 7,311,686 | B1 | 12/2007 | Iglesias et al. |
| 7,311,687 | B2 | 12/2007 | Hoffmeier et al. |
| D558,884 | S | 1/2008 | Ingimundarson et al. |
| D577,828 | S | 9/2008 | Ingimundarson et al. |
| 7,507,215 | B2 | 3/2009 | Ryan |
| 7,534,219 | B2 | 5/2009 | Stearns |
| 7,544,174 | B2 | 6/2009 | Nathanson |
| 7,578,799 | B2 | 8/2009 | Thorsteinsson et al. |
| 7,662,119 | B2 | 2/2010 | Detoro et al. |
| 7,682,322 | B2 | 3/2010 | Engelman |
| 7,699,798 | B2 | 4/2010 | Coligado |
| 7,722,555 | B2 | 5/2010 | Doty et al. |
| 7,749,183 | B2 | 7/2010 | Ingimundarson et al. |
| 7,762,972 | B2 | 7/2010 | Cho |
| 7,811,242 | B2 | 10/2010 | Seligman |
| 7,967,765 | B2 | 6/2011 | Nathanson |
| 7,985,193 | B2 | 7/2011 | Thorsteinsson et al. |
| 8,043,243 | B2 * | 10/2011 | Nathanson ............ A61F 5/0123 |
| | | | 602/26 |
| 8,048,013 | B2 | 11/2011 | Ingimundarson et al. |
| 8,062,242 | B2 * | 11/2011 | Ceriani ................ A61F 5/0123 |
| | | | 602/23 |
| 8,202,325 | B2 | 6/2012 | Albrecht-Laatsch et al. |
| 8,287,476 | B2 | 10/2012 | Bettiol |
| 8,292,838 | B2 * | 10/2012 | Ingimundarson ..... A61F 5/0123 |
| | | | 602/61 |
| 8,795,212 | B2 | 8/2014 | Seligman |
| 8,864,692 | B2 | 10/2014 | Ingimundarson et al. |
| 8,939,924 | B1 | 1/2015 | Paulos |
| 8,979,782 | B2 | 3/2015 | Romo et al. |
| 9,125,730 | B2 | 9/2015 | Ingimundarson et al. |
| 9,220,625 | B2 | 12/2015 | Ingimundarson et al. |
| 9,333,107 | B2 | 5/2016 | Potter et al. |
| 9,345,605 | B2 | 5/2016 | Dunn et al. |
| 9,668,903 | B2 * | 6/2017 | Hsu ...................... A61F 5/0125 |
| 9,788,986 | B2 | 10/2017 | Dunn |
| 10,588,770 | B2 | 3/2020 | Brookover et al. |
| 11,607,330 | B1 * | 3/2023 | Gaylord ................ A61F 5/0123 |
| 11,612,506 | B2 | 3/2023 | Johnson et al. |
| 12,102,549 | B2 * | 10/2024 | Gildersleeve ......... A61F 5/0123 |
| 2002/0107462 | A1 | 8/2002 | Freeman et al. |
| 2002/0107464 | A1 | 8/2002 | Castillo |
| 2002/0183674 | A1 | 12/2002 | Castillo |
| 2004/0002674 | A1 | 1/2004 | Sterling |
| 2004/0019949 | A1 | 2/2004 | Crockett |
| 2004/0054307 | A1 | 3/2004 | Mason et al. |
| 2004/0097859 | A1 | 5/2004 | Stearns |
| 2004/0167452 | A1 | 8/2004 | Mason et al. |
| 2005/0148915 | A1 | 7/2005 | Nathanson et al. |
| 2005/0148918 | A1 | 7/2005 | Nathanson |
| 2005/0165338 | A1 | 7/2005 | Iglesias et al. |
| 2005/0192523 | A1 | 9/2005 | Knecht et al. |
| 2006/0009722 | A1 | 1/2006 | Seligman |
| 2006/0100561 | A1 | 5/2006 | Gilmour |
| 2006/0135901 | A1 | 6/2006 | Ingimundarson et al. |
| 2006/0135903 | A1 | 6/2006 | Ingimundarson et al. |
| 2006/0167394 | A1 | 7/2006 | Ceriani et al. |
| 2006/0167396 | A1 | 7/2006 | Berger |
| 2006/0173392 | A1 | 8/2006 | Turrini et al. |
| 2006/0287624 | A1 | 12/2006 | Popp et al. |
| 2007/0225824 | A1 | 9/2007 | Einarsson |
| 2007/0293798 | A1 | 12/2007 | Hu et al. |
| 2008/0108922 | A1 | 5/2008 | Castillo et al. |
| 2008/0188784 | A1 | 8/2008 | Ceriani et al. |
| 2009/0030356 | A1 | 1/2009 | Maloney |
| 2009/0182254 | A1 | 7/2009 | Cho |

| | | | |
|---|---|---|---|
| 2009/0299244 | A1 * | 12/2009 | Chiang et al. |
| 2010/0049108 | A1 * | 2/2010 | Napholz ............... A61F 5/0123 |
| | | | 602/26 |
| 2010/0286579 | A1 | 11/2010 | Bettiol |
| 2011/0152736 | A1 | 6/2011 | Ng |
| 2012/0059296 | A1 | 3/2012 | Kompa |
| 2012/0271211 | A1 | 10/2012 | Bledsoe |
| 2013/0331754 | A1 | 12/2013 | Dunn et al. |
| 2014/0094351 | A1 | 4/2014 | Cersonsky |
| 2014/0207040 | A1 | 7/2014 | Ingimundarson et al. |
| 2014/0330393 | A1 | 11/2014 | Ward et al. |
| 2015/0038889 | A1 | 2/2015 | Mason et al. |
| 2015/0223958 | A1 | 8/2015 | Dunn |
| 2015/0267450 | A1 | 9/2015 | Chiang |
| 2015/0374530 | A1 | 12/2015 | Bosshard et al. |
| 2016/0008157 | A1 | 1/2016 | Brookover et al. |
| 2016/0038327 | A1 | 2/2016 | Mason et al. |
| 2016/0058596 | A1 | 3/2016 | Chiang et al. |
| 2016/0143763 | A1 | 5/2016 | Hsu et al. |
| 2016/0278947 | A1 | 9/2016 | Martin |
| 2017/0110937 | A1 | 4/2017 | Billings |
| 2017/0119569 | A1 | 5/2017 | Hsu et al. |
| 2017/0298981 | A1 | 10/2017 | Asgeirsson |
| 2018/0153711 | A1 | 6/2018 | Hsu et al. |
| 2019/0159919 | A1 * | 5/2019 | Turconi ................ A61F 5/0102 |
| 2020/0306070 | A1 * | 10/2020 | Hsu ....................... A61F 5/0102 |

FOREIGN PATENT DOCUMENTS

| | | |
|---|---|---|
| EP | 0070411 A1 | 1/1983 |
| EP | 0327286 A2 | 8/1989 |
| EP | 0382976 A1 | 8/1990 |
| EP | 0413424 A1 | 2/1991 |
| EP | 0454186 A2 | 10/1991 |
| EP | 0546330 A1 | 6/1993 |
| EP | 0615734 A1 | 9/1994 |
| EP | 0693276 A1 | 1/1996 |
| EP | 1010409 A1 | 6/2000 |
| EP | 1388330 A1 | 2/2004 |
| EP | 1639970 A2 | 3/2006 |
| EP | 1829507 A1 | 9/2007 |
| EP | 2345393 A1 | 7/2011 |
| EP | 2823792 A1 | 1/2015 |
| GB | 190626961 A | 4/1907 |
| WO | 90/14807 A1 | 12/1990 |
| WO | 99/39668 A1 | 8/1999 |
| WO | 01/10360 A1 | 2/2001 |
| WO | 2004/078078 A1 | 9/2004 |
| WO | 2009/092798 A1 | 7/2009 |
| WO | 2014/067698 A1 | 5/2014 |
| WO | 2015/157723 A1 | 10/2015 |
| WO | 2016/100791 A1 | 6/2016 |
| WO | 2017/075143 A1 | 5/2017 |

OTHER PUBLICATIONS

Innovation Sports, Products, Knee, OTS "Aspire", 1 page, available at least as early as Feb. 12, 2007.
Innovation Sports, Products, Knee, OTS "Edge", 1 page, available at least as early as Feb. 12, 2007.
Innovation Sports, Products, Knee, OTS "Morph", 1 page, available at least as early as Feb. 12, 2007.
Innovation Sports, Products, Knee, OTS "PCL", 1 page, available at least as early as Feb. 12, 2007.
International Search Report and Written Opinion from corresponding International PCT Application No. PCT/US2015/015358, Apr. 22, 2015.
International Search Report from corresponding International PCT Application No. PCT/US2013/043322, Aug. 20, 2013.
International Search Report from PCT Application No. PCT/US2015/061480, Apr. 4, 2016.
International Search Report From PCT Application No. PCT/US2017/027147, Jun. 26, 2017.
International Search Report from PCT Application No. PCT/US2017/064827, Feb. 26, 2018.
International Search Report from PCT No. PCT/US2016/059005, Jan. 5, 2017.

(56)  References Cited

OTHER PUBLICATIONS

National Cancer Institute—Anatomical Terminology (Year: 2022).
Plasticomp, "Material Data Sheet: PlastiComp Complet LCF40-
PA66 MT Nylon 66, 40% Long Carbon Fiber Reinforced, Impact
Modified", retrieved from https://www.matweb.com/search/datasheet.
aspxmatguid=9bd61390b68740f68669a46aeb6v5db9&ckck=1 on Nov.
20, 2024, 2 Pages.

* cited by examiner

HINGE ASSEMBLY

CROSS-REFERENCE TO RELATED APPLICATIONS

This application incorporates by reference the entirety of U.S. provisional application No. 63/605,261, filed on Dec. 1, 2023, US patent application publication no. 2017/0119569, published May 4, 2017, and US patent publication no. 2020/0306070, published Oct. 1, 2020.

TECHNICAL FIELD

The disclosure relates to a hinge assembly for orthopedic or prosthetic device use.

BACKGROUND

Many orthopedic devices include hinges supporting joints and controlling and limiting joint movements. Such joints include the knee, elbow, shoulder, hip, ankle, and wrist joints. For example, the knee joint comprises two lateral and medial joints between the femur and tibia and one arthrodial joint between the patella and femur. The primary movements of the knee comprise flexion (i.e., rearward rotational movement of the tibia relative to the femur) and extension (i.e., forward rotational movement of the tibia relative to the femur).

The flexion and extension movements of the knee joint are not pivotal movements about a fixed axis. Instead, the axis around which movement occurs shifts backward during flexion and extension, and the axis shifts forward. This movement differs from a more typical hinge joint, such as an elbow, where the axis of rotation does not shift during movement.

Because of the complexity associated with knee movement, which is further outlined in US patent publication no. 2020/0306070, a knee-brace hinge must be able to simulate the complex anatomical movements of the knee and must optimally support the knee joint of its user throughout the normal range of motion and use for increased comfort, compliance, and efficacy. The knee-brace hinge should also assist in applying loads to the knee that will improve the healing of injuries or relief from osteoarthritic complications and improve comfort for and compliance by a user.

The inventors of the present disclosure have identified that existing knee-brace hinges lack long-term durability for use with an orthopedic device. Over time, the flexion and extension movements at the point of contact of knee-brace hinges degrade hinge parts and damage the gears. The damage and degradation of hinge parts can lead to misalignment of the orthopedic device and injure the user. Thus, there is a need for a hinge assembly with improved durability to withstand constant flexion and extension movements at the knee joint.

Existing orthopedic devices have used the advantageous material properties of carbon fiber. Carbon fiber material has several advantages: high stiffness, high strength-to-weight ratio, high tensile strength, high chemical resistance, high-temperature tolerance, and low thermal expansion. However, the inventors of the present disclosure observed that hinge assemblies with carbon fiber gears in direct contact with other carbon fiber gears can lead to ground-down gears and worn hinge walls. This direct carbon-carbon contact results in excess debris. Collected debris can degrade the hinge assembly and supporting structures, thus reducing the overall effectiveness and lifespan of the orthopedic device.

Collected debris can also create discomfort and unnecessary pressure points. Thus, there is a need for a hinge assembly that avoids the buildup and entrapment of debris.

SUMMARY

The embodiments of the disclosure are arranged to overcome the drawbacks in hinge assemblies of the prior art.

Hinge assembly embodiments described herein are adapted to provide improved durability over hinge assemblies in the prior art by incorporating a distinct wear insert. The hinge assembly can be adapted for orthopedic devices, prosthetic devices, other devices, and other joints.

According to an embodiment of a hinge assembly for an orthopedic device of the disclosure, the hinge assembly comprises a first hinge arm with a first end portion and a second hinge arm with a second end portion. A wear insert is integrated within a thickness of the second end portion and is configured and dimensioned to mesh and interact with a gear segment defined by the first end portion. The gear segment of the first end portion is integrally formed from the first hinge arm and is formed with the same material as the first hinge arm. The wear insert of the second end portion is distinctly formed from the second hinge arm. Distinctly formed means that the wear insert is composed of a material different from the material forming the second hinge arm, and/or is formed separately from the second hinge arm. The second end portion may be an overmold over a portion of the wear insert.

The first end portion comprises a bushing that coincides with the first radius of the gear segment and defines a first wear surface. The bushing is composed of a different material from the first end portion. The bushing is preferably composed of a thermoplastic material such as nylon. The bushing forms an inner flange and an outer flange that project beyond opposing sides of the first end portion. The flanges provide improved wear surfaces on opposing sides of the first end portion to reduce a grinding effect and prevent misalignment of the hinge assembly.

The gear segment of the first end portion defines a first set of teeth composed of the same material as the first hinge arm. The wear insert defines a second set of teeth configured to cooperate and form an interface. The second set of teeth is composed of a material different from the first set of teeth to reduce the grinding effect and prevent misalignment of the hinge assembly. In a preferred embodiment, the wear insert consists of a thermoplastic material such as nylon.

The second set of teeth of the wear insert form rounded caps at the gear tips to cooperate with the first set of teeth. The rounded caps (i.e., radii) offer a more forgiving shape regarding misalignment of the hinge assembly while preventing slippage and allowing motion and power transmission between arms and frame components. The second set of teeth of the wear insert further defines slots formed at the gear roots to collect debris. Slopes extending from the slots toward opposing sides of the wear insert are configured and dimensioned to eject the debris beyond opposing sides of the second end portion. The slots prevent the accumulation of debris to increase the overall effectiveness and lifespan of the orthopedic device.

In an embodiment, the wear insert forms at least one aperture through which the material of the second end portion extends to interlock the wear insert with the second end portion. In an embodiment, the wear insert forms at least one radial projection embedded within the second end portion.

In an embodiment, the wear insert forms at least one extended wear surface (i.e., flange) on opposing sides of the second end portion. The extended wear surface of the wear insert provides improved wear surfaces on opposing sides of the second end portion to reduce a grinding effect and prevent misalignment of the hinge assembly.

The wear insert further defines a second wear surface that coincides with a second radius of the wear insert. The first and second end portions are connected by at least one cover that interfaces with the first and second wear surfaces. The at least one cover is connected to the first and second wear surfaces by fastening means (e.g., screw and nut) to facilitate hinge rotation while preventing movement in a direction perpendicular to the rotational axis (or axes) of the joint.

These and other features, aspects, and advantages of the present disclosure will be better understood in the following description, appended claims, and accompanying drawings.

BRIEF DESCRIPTION OF THE DRAWINGS

The drawing figures are not necessarily drawn to scale but instead are drawn to provide a better understanding of the components thereof. They are not intended to limit scope but to provide exemplary illustrations. The figures illustrate exemplary configurations of the hinge assembly and in no way limit the structures or configurations according to the present disclosure.

DETAILED DESCRIPTION OF VARIOUS EMBODIMENTS

A. Overview

Figure 1:
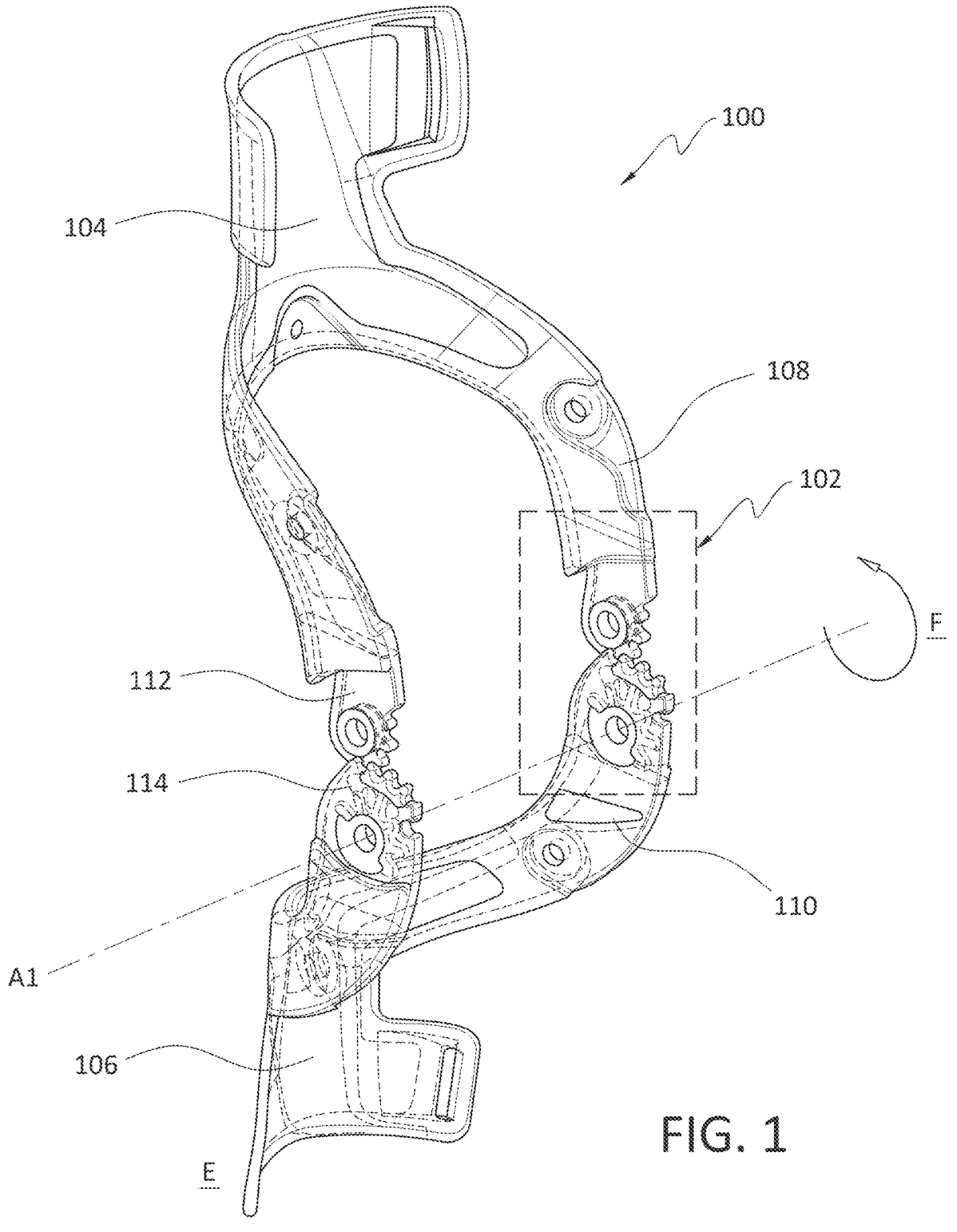
FIG. 1 is a perspective view of a hinge assembly in an orthopedic device according to an embodiment of the disclosure.

A better understanding of different embodiments of the disclosure may be had from the following description read with the accompanying drawings in which reference characters refer to elements.

While the disclosure is susceptible to various modifications and alternative constructions, certain illustrative embodiments are in the drawings and are described below. It should be understood, however, that there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

B. Environment and Context of Embodiments

Numerous orthopedic device embodiments and components (e.g., subshells and strap retainers) are described herein, focusing on braces and components directed to the knee joint and surrounding areas. The orthopedic brace embodiments may serve in protective, preventive, or remedial capacities. While the orthopedic brace is described within the context of a preferred embodiment directed to securing the knee joint, many features described herein may be extended to orthopedic braces and components that secure other joints and body parts, such as the wrist, elbow, shoulder, ankle, and neck.

The brace embodiments and components for use therewith may be dimensioned to accommodate different types, shapes, and sizes of human joints and appendages. In addition, embodiments may be modified to orient principal forces exerted by strap systems at any desirable location to secure the brace onto a leg to stabilize the knee.

The knee joint comprises two joints, lateral and medial, between the femur and tibia and one arthrodial joint between the patella and femur. The primary movements of the knee comprise flexion, i.e., rearward rotational movement of the tibia relative to the femur, and extension, i.e., forward rotational movement of the tibia relative to the femur.

For explanatory purposes, each orthopedic brace embodiment or component thereof described may be divided into sections denoted by general anatomical terms for the human body. Such anatomical terms are provided to distinguish various elements of the brace embodiments from one another, but which are not to be considered to limit the scope of the invention.

C. Various Embodiments and Components for Use Therewith

Numerous hinge assembly embodiments are described herein, focusing on the knee joint and surrounding areas. The hinge assembly embodiments may serve in protective, preventive, or remedial capacities. While the hinge assembly is described within the context of a preferred embodiment directed to treating the knee, many features described may be extended to orthopedic devices and components that secure other joints and body parts. It should be appreciated that the hinge assembly embodiments may be dimensioned to accommodate different types, shapes, and sizes of human joints and appendages. It should also be appreciated that the hinge assembly can be adapted for prosthetic devices, medical devices, or other devices.

As understood below, the hinge assembly is a "polycentric" hinge commonly understood in orthopedic braces, which includes a pair of rigid support arms having cooperating, interlocking proximal ends, a pair of pivot pins, and a hinge plate. The arms are rotatably coupled at their proximal ends to the hinge plate through the pivot pins and are rotatable between an adjustable extension position and an adjustable flexion position. An example of a polycentric hinge is described in U.S. Pat. No. 5,443,444, which is incorporated herein by reference.

FIG. 1 illustrates an orthopedic device 100 comprising a hinge assembly 102 on both medial and lateral sides of the device 100. The orthopedic device 100 is shown to be in an extension E position. Shifting the axis A1 along the arrow suggests that the orthopedic device 100 may be moved into a flexion F position. As depicted, the orthopedic device 100 is a knee brace having a first frame member 104 and a second frame member 106. The first frame member 104 is configured to support an upper leg of a user. The second frame member 106, arranged below or distal to the first frame member 104, is configured to support a user's lower leg. Using a strap system (not shown), the first frame member 104 and second frame member 106 may be secured to an anterior side of the user's leg. The first frame member 104 forms a first hinge arm 108 of the hinge assembly 102. The first hinge arm 108 comprises a first end portion 112 to form a proximal part of the hinge assembly 102. The second frame member 106, forms a second hinge arm 110 of the hinge assembly 102. The second hinge arm 110 comprises a second end portion 114 to form a distal part of the hinge assembly 102.

The first and second frame members 104, 106 are preferably constructed from long fiber reinforced thermoplastic materials to achieve the desired characteristics of a balance of sufficient rigidity and flexibility and lightweight on a mass scale suitable for off-the-shelf braces. By being "long fiber," the fibers are defined as individual reinforcing fibers with a uniform length and parallel alignment. For example, the individual reinforcing fibers are aligned with each other and are generally exactly as long as a pellet used in the injection molding process. In comparison, short fiber reinforced thermoplastic materials contain reinforcing fibers of various short lengths randomly oriented in the resin pellet.

The preferred embodiments of the first and second frame members 104, 106 are formed from long-fiber individual reinforcing fibers, which enable the first and second frame members 104, 106 to have superior and predictable mechanical performance compared to short-fiber reinforced thermoplastic materials. An exemplary long fiber reinforced thermoplastic material is provided by Plasticomp LLC of Winona, Minn., under the product name Complēt LCF40-PA66 M T 1014 NAT. The product uses a thermoplastic resin of Nylon 66, and the long fiber is carbon, with a fiber content of 40%.

From the long fiber individual reinforcing fibers and due to the injection molding process of the thermoplastic resin, the material properties of the first and second frame members 104, 106 have improved material properties, such as tensile and impact strength, weight and dimensional stability, and with discrete zones of relative enhanced rigidity (i.e., struts, central segment, and masts) relative to other zones (as in the medial and lateral arms). The long fiber-reinforced thermoplastic material forming the first frame member 104 forms an improved bearing surface, which enables the first hinge arm 108 to be formed from the first and second frame components, as opposed to using metal inserts commonly found in knee braces constructed from thermoset resin impregnated carbon fiber. The second frame member 106 and the second hinge arm 110 may also be formed of the long fiber reinforced thermoplastic material; however, as will be explained in greater detail below, the second hinge arm 110 includes a wear insert 122 that is constructed of a different material than the first and second hinge arms 108, 110.

In an embodiment, the first and second frame members 104 106 are injection molded to shape so that minimal post-mold finish work is necessary. The first and second frame members 104 106 are preferably molded into a definitive shape, so minimal or no sanding, bonding, or paint is required. By molding the shapes from an initial definitive mold, there is a high degree of freedom in initially shaping the first and second frame members 104, 106.

Figure 2:
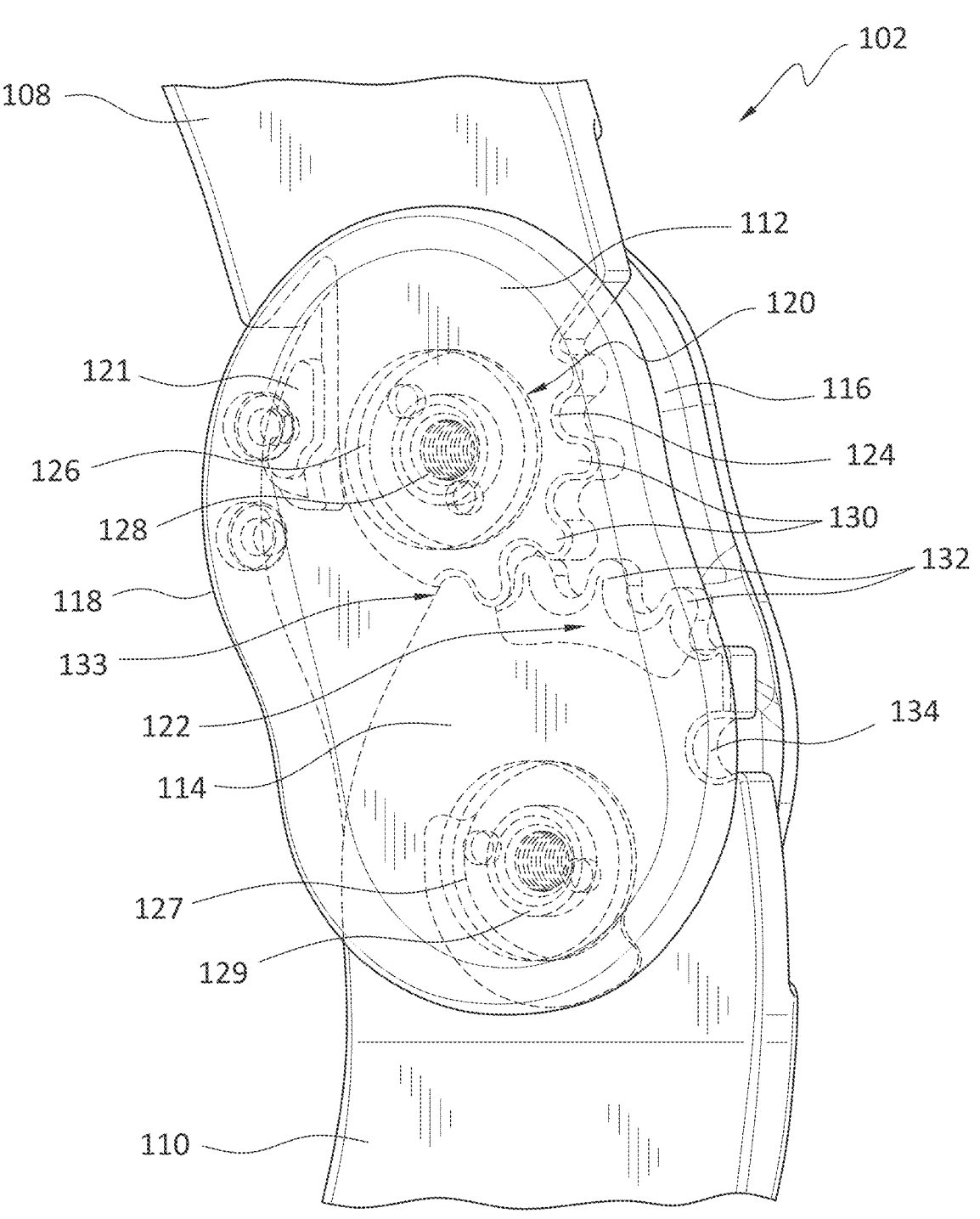
FIG. 2 is a perspective view of the hinge assembly.

FIG. 2 illustrates an embodiment of the disclosed hinge assembly 102. The hinge assembly 102 is created at the junction of the first end portion 112 of the first hinge arm 108 and the second end portion 114 of the second hinge arm 110. The hinge assembly 102 preferably comprises a first cover 116 and a second cover 118 to prevent misalignment and movement in the peripheral (i.e., lateral and medial) directions. The cover 116 may include an extension stop 121 and be configured and dimensioned to cooperate with the hinge assembly similar to the covers and plates described in US patent publication no. 2020/0306070. The first and second covers 116, 118 are used to retain the first and second end portions 112, 114 as connected, aside from their preferable geared profiles. The first and second covers 116, 118 are secured to the first and second end portions 112, 114 by male fasteners 126, 127 being interlocked with female fasteners 128, 129. In an embodiment, the male fasteners 126, 127 are titanium or steel screws and the female fasteners 128, 129 are titanium or steel nuts configured and dimensioned to receive the male fasteners 128, 129, respectively. Rotation about the male and female fasteners 126, 127, 128, 129 is enabled by the bushing 120 of the first end portion 112 and the wear insert 122 of the second end portion 114.

The first end portion 112 comprises gear segment 124 having a first set of teeth 130 to engage with a second set of teeth 132 of the wear insert 122. The first set of teeth 130 and the second set of teeth 132 are arranged to cooperate and form an interface 133. The interface 133 is a cooperative mechanism that meshes the sets of teeth 130, 132 together to transmit rotary motion from one arm 108, 110 to another. The number of teeth for each set varies depending on the application. In an embodiment, the first set of teeth 130 and the second set of teeth 132 preferably form an identical amount or number of teeth. The teeth of the first and second end portions 112, 114 are preferably similarly sized. The teeth may be formed only about a limited periphery of the interfacing first and second end portions 112, 114.

Figures 3A, 3B:
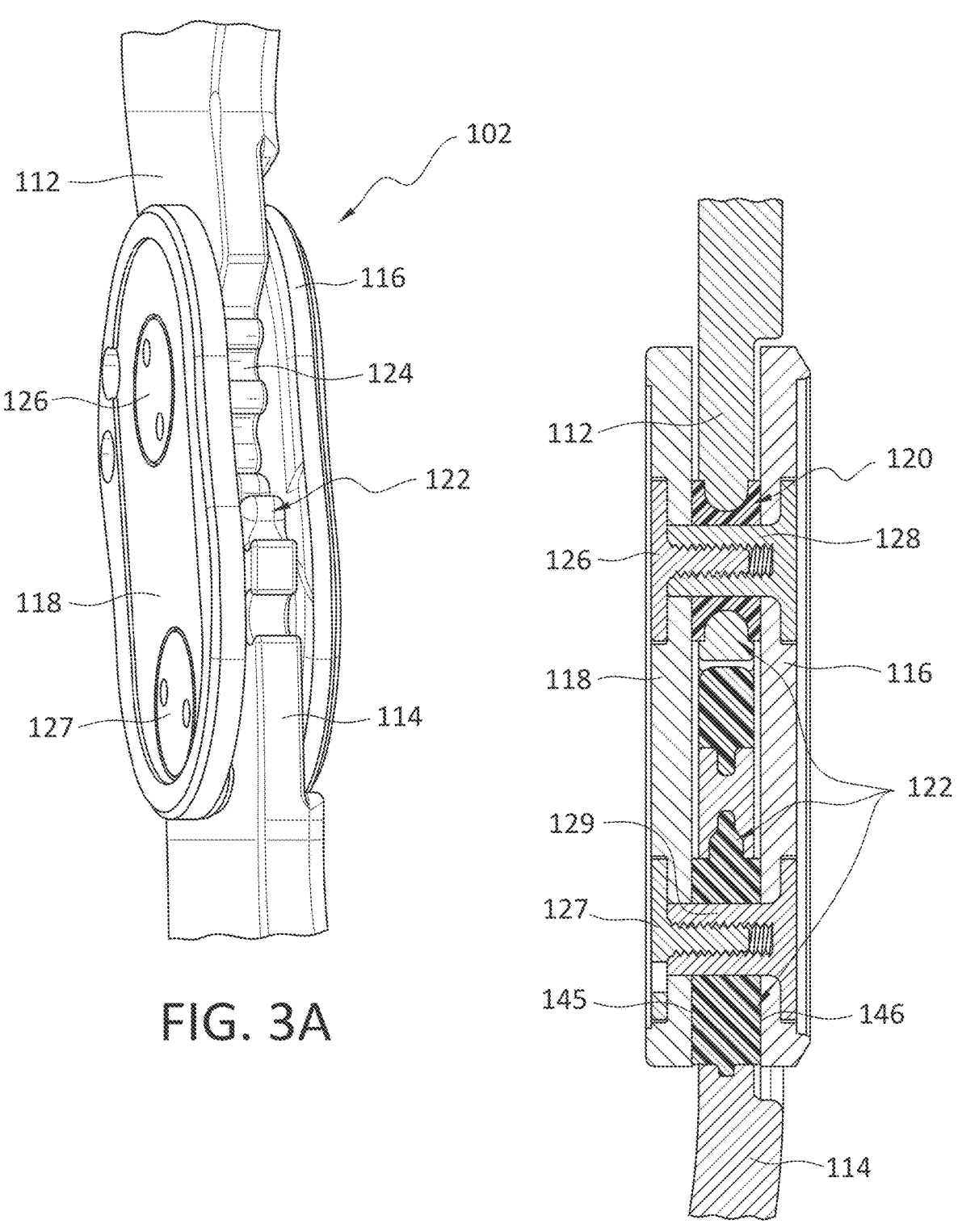
FIGS. 3A-3B are sectional perspective views of the hinge assembly of FIG. 2.

FIGS. 3A and 3B illustrate alternative views of the hinge assembly 102 from FIG. 2. The first end portion 112 and second end portion 114 are retained between the first cover 116 and the second cover 118. The first cover 116 and the second cover 118 extend over both peripheral sides of the first and second end portions 112, 114; thus, the covers 116, 118 extend over the formed interface 133. The male fasteners 126, 127 that extend through the second cover 118 mate with the female fasteners 128, 129 that extend through the first cover 116.

Referred to FIG. 3B, the wear insert 122 is observed as being integrated within a thickness of the second end portion 114. The term "integrate" generally refers to a process in which material is molded or cast onto another material that may be composite, metal, or polymer in nature. The result of the wear insert 122 being integrated with the second end portion 114 is a single, integrated component of two different materials, which generally have distinct functions in the hinge assembly 102. The wear insert 122 comprises extended wear surfaces 145, 146 that extend to or beyond the peripheral sides of the second end portion 114. The extended wear surfaces 145, 146 reduce a grinding effect on the inner surfaces of the covers 116, 118 against the second end portion 114. In embodiments wherein the wear insert consists of a thermoplastic material, such as nylon, and the first and second frame members 104, 106 comprise carbon fiber material, the extended wear surfaces 145, 146 reduce or eliminate carbon-carbon surface contact to prevent the creation of carbon debris.

Figures 4, 5:
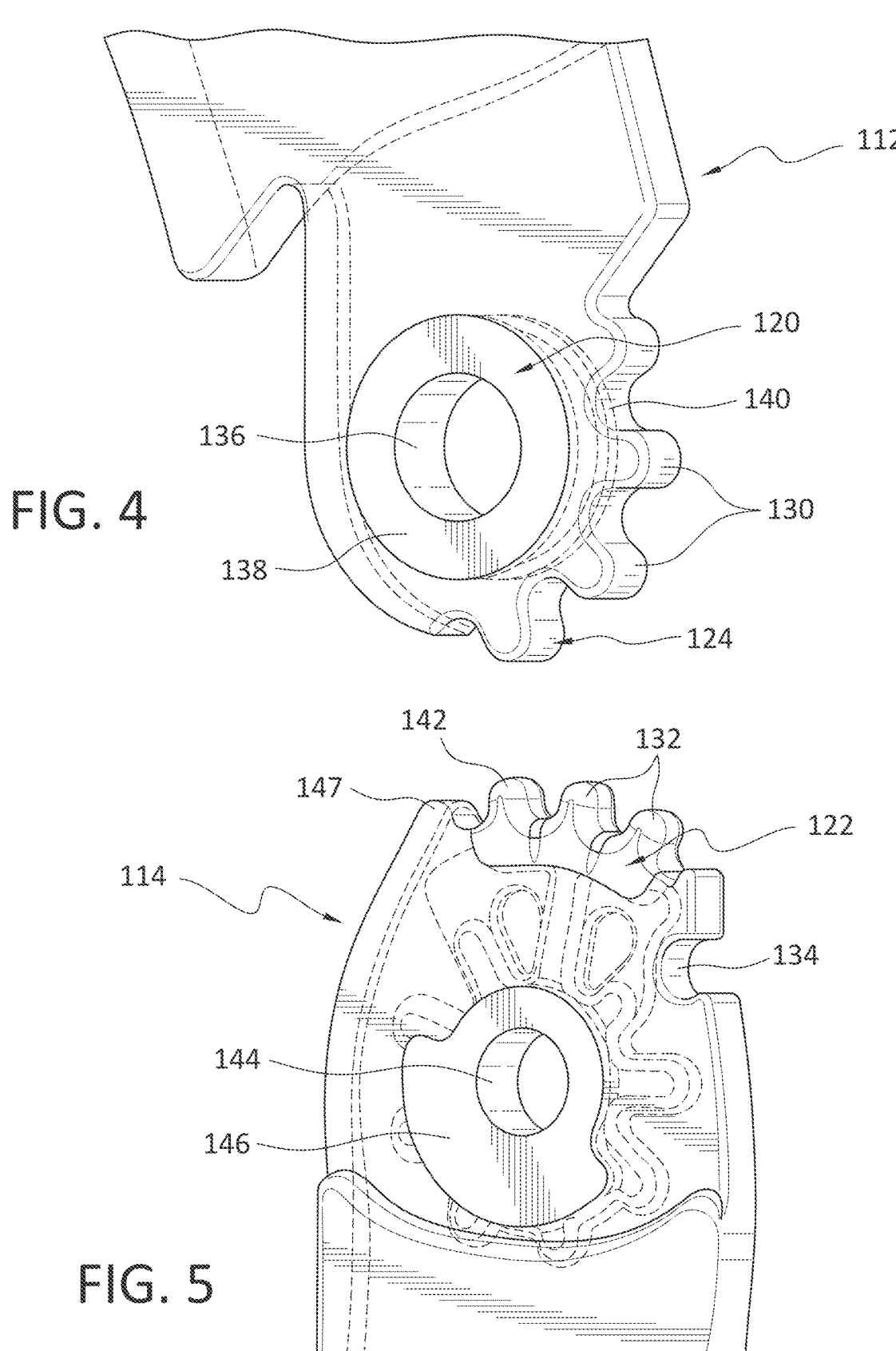
FIG. 4 is a perspective view of the first end portion and bushing of the present disclosure.
FIG. 5 is a perspective view of the second end portion and wear insert of the present disclosure.

FIG. 4 illustrates a perspective view of the first end portion 112 comprising a bushing 120. The bushing 120 is preferably composed of a thermoplastic material such as nylon. The internal surface of the bushing 120 is defined as a first-wear surface 136. The first wear surface 136 contacts a corresponding female fastener (e.g., female fastener 128) and supports rotation of the first end portion 112 about respective fasteners (e.g., male fastener 126 and female fastener 128). The bushing 120 forms an inner flange 138 and an outer flange 140 that project beyond opposing sides of the first end portion 112. The first wear surface 136 is the barrel portion of the bushing 120 that extends from the inner flange 138 to the outer flange 140. The flanges 138, 140 provide improved wear surfaces on opposing sides of the first end portion 112 to reduce a grinding effect and prevent misalignment of the hinge assembly 102.

The gear segment 124 is configured and dimensioned to, at least partially, radially extend about the bushing 120. The gear segment 124 of the first end portion 112 defines a first set of teeth 130 that are composed of the same material as the first hinge arm 108 and the first end portion 112. The bushing is preferably formed as a monolithic material, wherein the first end portion 112 is overmolded about the bushing 120 to form an integral connection. By forming the bushing 120 into the first end portion 112, (e.g., being overmolded with 40% carbon-filled nylon), the flanges 138, 140 form wear surfaces that comprise a different material from the first hinge arm 108 and first end portion 112.

FIG. 5 illustrates a perspective view of the second end portion 114 comprising the wear insert 122. As observed, the second end portion 114 comprises a receptacle 134 to accommodate a flexion stop, similar to that described in US patent publication no. 2020/0306070. The wear insert 122 defines a second set of teeth 132 that are configured and arranged to cooperate with the first set of teeth 130. The second set of teeth 132 is composed of a material different from the first set of teeth 130, which reduces the grinding effect and prevents misalignment of the hinge assembly 102. In a preferred embodiment, the wear insert 122 consists of a thermoplastic material such as nylon. In an embodiment, the second end portion 114 may comprise one or more peripheral teeth 147 in addition to the second set of teeth 132 provided by the wear insert 122. The peripheral teeth 147 may be formed of the same material as the second hinge arm. In an embodiment, the second set of teeth 132 form all teeth configured and dimensioned at the second end portion 114 to interface with the first set of teeth 130.

In the illustrated embodiment, the wear insert 122 is held in place by the second end portion 114, which is molded or overmolded at least over a portion of the wear insert 122. The term "overmold" has its ordinary meaning and refers to the material added to an existing article or material. Overmolding is generally understood as a process where a single part is created using two or more different materials in combination. In the instant disclosure, the interlocked structure formed by the wear insert 122 and a second end portion 114 may be considered such a single part.

As mentioned above, the wear insert 122 further comprises extended wear surfaces 145, 146 that extend beyond peripheral sides of the second end portion 114 and interact with the covers 116, 118. The extended wear surfaces 145, 146 provide improved wear surfaces on opposing sides of the second end portion 114 to reduce a grinding effect and prevent misalignment of the hinge assembly 102. The internal surface of the wear insert 122 is defined as a second wear surface 144. The second wear surface 144 contacts a corresponding female fastener (e.g., female fastener 129) and supports rotation of the second end portion 114 about respective fasteners (e.g., male fastener 127 and female fastener 129).

Figure 6:
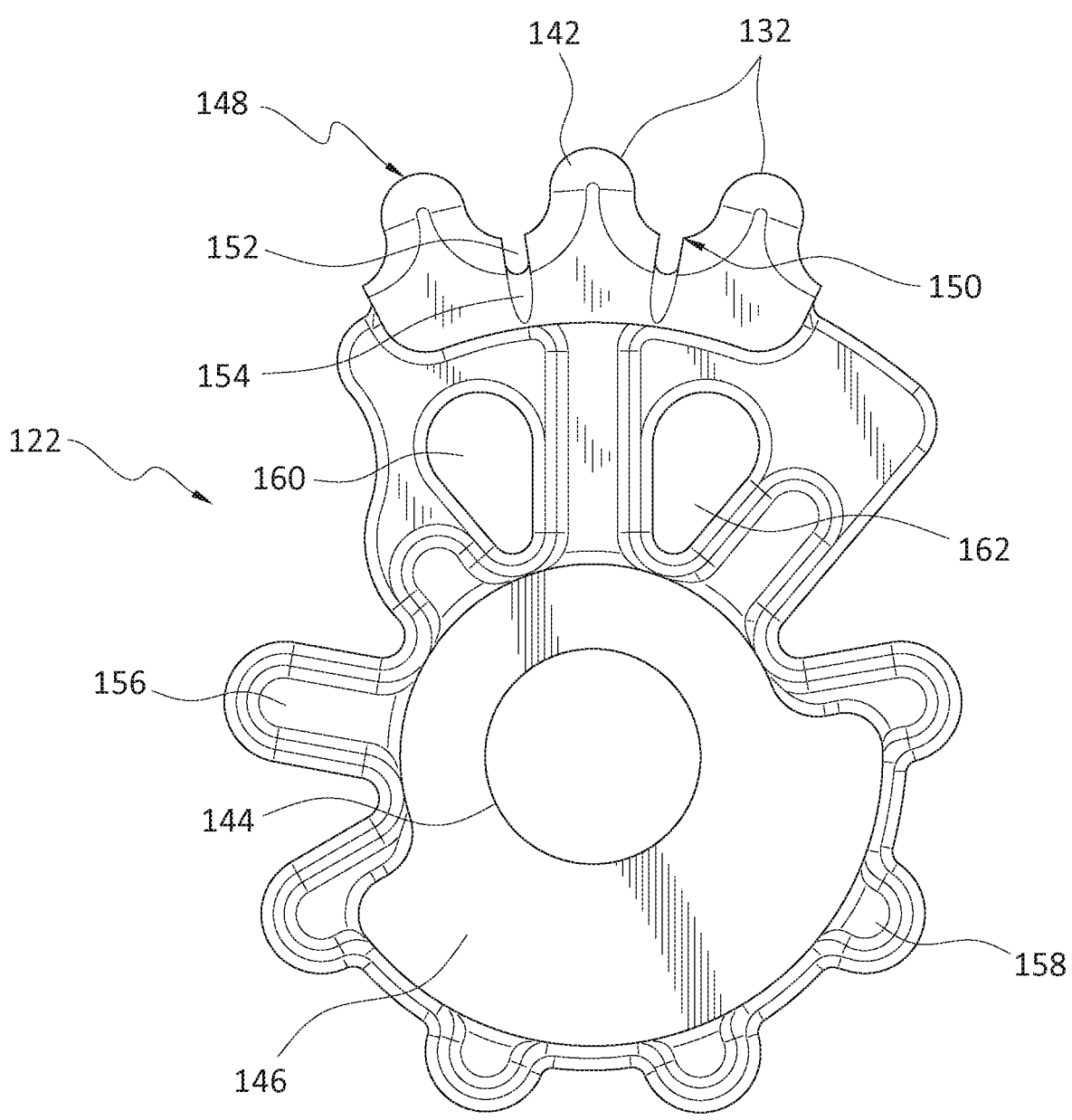
FIG. 6 is a side elevational view of the wear insert according to an embodiment of the present disclosure.

FIG. 6 depicts a side view of the wear insert 122. The term "wear insert" generally refers to a monolithic gear element having an arcuate, toothed configuration to cooperate with an opposing gear segment. As noted above, the second set of teeth 132 of the wear insert 122 is composed of a material different from the first set of teeth 130 to reduce the grinding effect and prevent misalignment of the hinge assembly 102. In a preferred embodiment, the wear insert 122 consists of a thermoplastic material such as nylon. The second set of teeth 132 preferably comprise rounded caps 142 defined on each gear tip 148. The rounded caps 142 allow for a more forgiving shape concerning misalignment of the hinge assembly 102, preventing slippage and allowing transmission of motion and power between arms and frame components. The second set of teeth 132 of the wear insert further defines slots 152 formed at the gear roots 150 to collect debris. Slopes 154 extending from the slots 152 toward opposing sides of the wear insert 122 are configured and dimensioned to eject the debris beyond opposing sides of the second end portion 114. The slots 152 prevent the accumulation of debris to increase the overall effectiveness and lifespan of the orthopedic device 100.

In an embodiment, the wear insert 122 forms at least one aperture 160, 162 through which material of the second end portion 114 extends to interlock the wear insert 122 with the second end portion 114. The apertures 160, 162 facilitate a secure connection and improved mechanism for overmolding the second end portion 114 to link with the wear insert 122. In an embodiment, the wear insert 122 forms at least one radial projection 156, 158 that can be embedded within the second end portion 114. The radial projections 156, 158 may form ridges, flanges, or other protrusions to enhance the embeddedness of the wear insert 122 with the second end portion 114.

It is understood that not all objects or advantages may be achieved under any embodiment of the disclosure. Those skilled in the art will recognize that the hinge may be embodied or carried out in a manner that achieves or optimizes one advantage or group of advantages as taught herein without achieving other objects or advantages as taught or suggested herein.

The skilled artisan will recognize the interchangeability of various disclosed features. Besides the variations described herein, other known equivalents for each feature can be mixed and matched by one of ordinary skill in this art to build and use the hinge under the principles of the present disclosure. The skilled artisan will understand that the features described herein may be adapted to other methods and types of hinges.

It is intended that the present disclosure should not be limited by the disclosed embodiments described above and may be extended to other applications that may employ the features described herein.

The invention claimed is:

1. A hinge assembly comprising:
   a first hinge arm having a first end portion;
   a second hinge arm having a second end portion;
   a wear insert arranged within a thickness of the second end portion;
   wherein the first end portion defines a gear segment formed from the first hinge arm and composed of a first material, and the wear insert of the second end portion is distinctly formed from the second hinge arm, the second hinge arm being composed of the first material and the wear insert being formed of a second material;
   wherein the gear segment defines a first set of teeth, and the wear insert defines a second set of teeth, the first and second sets of teeth arranged to cooperate with one another and form an interface.

2. The hinge assembly of claim 1, wherein the wear insert consists of a thermoplastic material different from the first material.

3. The hinge assembly of claim 2, wherein the thermoplastic material is nylon.

4. The hinge assembly of claim 1, wherein the first end portion comprises a bushing coinciding with a first radius of the gear segment and defining a first wear surface.

5. The hinge assembly of claim 4, wherein the bushing consists of a thermoplastic material and forms an inner flange and an outer flange projecting beyond opposing sides of the first end portion.

6. The hinge assembly of claim 1, wherein the second set of teeth form rounded caps at gear tips of the wear insert and are configured to cooperate with the first set of teeth.

7. The hinge assembly of claim 1, wherein the second set of teeth define slots formed at gear roots of the wear insert.

8. The hinge assembly of claim 7, wherein the slots include slopes configured to eject debris beyond opposing sides of the second end portion.

9. The hinge assembly of claim 4, wherein the wear insert defines a second wear surface coinciding with a second radius of the wear insert.

10. The hinge assembly of claim 1, wherein the first end portion and the second end portion are connected by at least one cover.

11. The hinge assembly of claim 1, wherein the wear insert forms at least one aperture through which material of the second end portion extends to interlock the wear insert with the second end portion.

12. The hinge assembly of claim 1, wherein the wear insert forms at least one extended wear surface on opposing sides of the second end portion.

13. A hinge assembly comprising:

a first hinge arm having a first end portion;

a second hinge arm having a second end portion;

a wear insert integrated within a thickness of the second end portion;

wherein the first end portion defines a gear segment integrally formed from the first hinge arm and composed of a first material, and the wear insert of the second end portion is distinctly formed from the second hinge arm, the second hinge arm being composed of the first material and the wear insert being formed of a second material;

wherein the gear segment defines a first set of teeth, and the wear insert defines a second set of teeth, the first and second sets of teeth arranged to cooperate with one another and form an interface;

wherein the second set of teeth form rounded caps at gear tips of the wear insert configured to cooperate with the first set of teeth.

14. The hinge assembly of claim 13, wherein the second set of teeth define slots formed at gear roots of the wear insert to collect debris.

15. The hinge assembly of claim 13, wherein the wear insert defines a second wear surface coinciding with a second radius of the wear insert.

16. The hinge assembly of claim 13, wherein the wear insert forms at least one aperture through which material of the second end portion extends to interlock the wear insert with the second end portion.

17. The hinge assembly of claim 13, wherein the wear insert forms at least one extended wear surface on opposing sides of the second end portion.

18. The hinge assembly of claim 13, wherein the wear insert forms at least one radial projection embedded within the second end portion.

19. A hinge assembly comprising:

a first hinge arm having a first end portion;

a second hinge arm having a second end portion;

a wear insert integrated within a thickness of the second end portion;

wherein the first end portion defines a gear segment integrally formed from the first hinge arm and composed of a first material, and the wear insert of the second end portion is distinctly formed from the second hinge arm, the second hinge arm being composed of the first material and the wear insert being formed of a second material;

wherein the gear segment defines a first set of teeth and the wear insert defines a second set of teeth, the sets of teeth being arranged to cooperate with one another and form an interface;

wherein the first end portion comprises a bushing coinciding with a first radius of the gear segment and defining a first wear surface, the bushing consisting of a thermoplastic material and forming an inner flange and an outer flange projecting beyond opposing sides of the first end portion.

* * * * *